United States Patent [19]

Müller

[11] 4,046,816

[45] Sept. 6, 1977

[54] PROCESS FOR PREPARING RESORCINOL MONOETHERS

[75] Inventor: Werner Heinrich Müller, Aldersbach, Germany

[73] Assignee: Hoechst Aktiengesellschaft, Frankfurt am Main, Germany

[21] Appl. No.: 586,352

[22] Filed: June 12, 1975

[30] Foreign Application Priority Data

June 14, 1974 Germany .......................... 2428879

[51] Int. Cl.$^2$ .......................................... C07C 41/00
[52] U.S. Cl. ........................ 260/613 R; 260/586 R; 260/571
[58] Field of Search .......... 260/613 D, 613 R, 621 H

[56] References Cited

U.S. PATENT DOCUMENTS

| | | | |
|---|---|---|---|
| 3,259,639 | 7/1966 | Taub | 260/613 D X |
| 3,801,651 | 4/1974 | Adolphen et al. | 260/613 D |
| 3,819,719 | 6/1974 | McKague et al. | 260/613 D |

OTHER PUBLICATIONS

Charonnat et al., Bull. Soc. Chim. France, (1949), pp. 209-211.
Treibs et al., Journal Fur Praktische Chemie, vol. 8, (1959) pp. 123-131.

*Primary Examiner*—Bernard Helfin
*Attorney, Agent, or Firm*—Curtis, Morris & Safford

[57] ABSTRACT

Process for the preparation of resorcinol monoalkyl ethers by dehydrogenizing 3-alkoxycyclohexene-(2)-ones in the liquid or gaseous phase.

1 Claim, No Drawings

PROCESS FOR PREPARING RESORCINOL MONOETHERS

The present invention relates to a new process for preparing resorcinol monoalkyl ethers. Said ethers have been prepared hitherto by monoalkylation of the corresponding resorcinols with alkylation agents such as alkyl halides or dialkyl sulfates. Said processes have the great disadvantage that condiderable quantities of salts are necessarily obtained and furthermore undesired dialkyl ethers, which signifies a loss of resorcinol and alkylation agent as well as a considerable waste water generation.

The resorcinol monoalkyl ehters are important organic intermediates, for example, as coupling components for dyestuffs, for example in the diazoprinting. They are furthermore intermediates for the synthesis of pesticides.

A process has now been found for the preparation of resorcinol monoalkyl ethers of the general formulae I and II

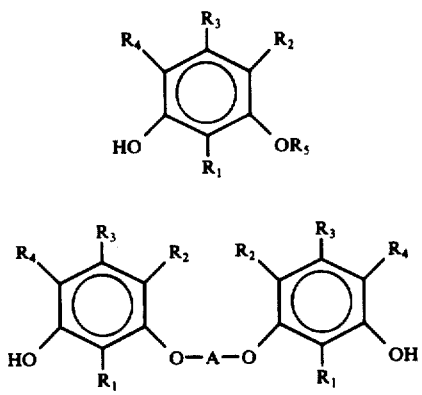

wherein the radicals $R_1$ to $R_4$ may be the same or different and each represent hydrogen, straight chain, branched or cyclic aliphatic radicals which may be substituted or aryl groups which may also be substituted or araliphatic radicals and the radicals $R_5$ and A represent straight chain, branched or cyclic aliphatic radicals or araliphatic radicals which may be substituted, which comprises dehydrogenizing 3-alkoxycyclohexene-(2)-ones(1) of the general formulae I' and II'

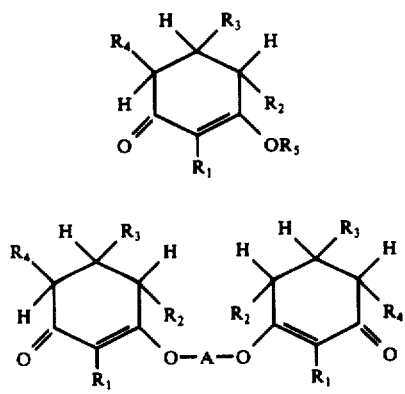

wherein $R_1$ to $R_5$ and A have the aforesaid meaning.

I' is the starting compound for I and II' the starting compound for II.

The straight chain, branched or cyclic aliphatic radicals suitable for $R_1$ to $R_5$ preferably have up to 12 carbon atoms. There may be mentioned, by way of example, methyl, ethyl, propyl, butyl, pentyl, hexyl, octyl, dodecyl, cyclohexyl, cyclododecyl. The aliphatic radicals may contain multiple bonds, such as the allyl group. The aliphatic radicals may moreover be substituted, for example, by halogen, especially fluorine and chlorine, or by amino, hydroxyl, keto, carboxy, carbamide or cyano groups, furthermore by an alkoxy or carbalkoxy group having up to 6 carbon atoms.

Aryl groups which may be used for the radicals $R_1$ to $R_4$ preferably are the phenyl or naphthyl group. The aryl groups may be substituted, for example, by halogen, especially fluorine and chlorine, by alkyl groups having up to 6 carbon atoms or by trifluoromethyl, pentafluoroethyl, amino, hydroxy or nitro groups. Alkoxy groups having up to 6 carbon atoms such as the methoxy or ethoxy group are also convenient.

Suitable araliphatic radicals for $R_1$ to $R_5$ preferably are such having from 1 to 4 carbon atoms in the aliphatic moiety and having the phenyl radicals as aromatic radical, for example, the benzyl radical and the phenylethyl radical.

For group A there may be used alkylene radicals having up to 12 carbon atoms such as $-(CH_2)_n-$, $n$ being 2,3,4,5,6,10,12

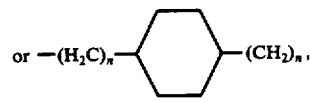

$n$ being 1,2 or the group

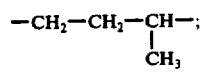

alkylene-arylene-alkylene-radicals such as, for example,

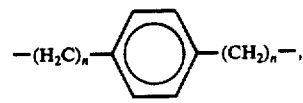

$n$ being 1,2. A may further stand for the following groups: $-CH_2-CH_2-(O-CH_2-CH_2)_n-OCH_2-CH_2-$, $n$ being 0,1. This is the case for example when cyclohexanediones are reacted with diglycol $HO-CH_2-CH_2-O-CH_2-CH_2-OH$ or with triglycol in order to obtain the starting product II' of the process according to the invention. Finally there may be used for A, for example, groups of the following type: $-H_2C-(CH=CH)_n-$ or $-H_2C-(C\equiv C)_n-CH_2-$, $n$ being 1 or 2.

The dehydrogenation of the 3-alkoxycyclohexenones may be effected by known methods, for example by reacting them with a dehydrogenation agent such as sulfur or selenium or by heating it in the presence of a dehydrogenation catalyst.

Suitable dehydrogenation catalysts for such a catalytic dehydrogenation, for example, are those of the group of the platinum metals, i.e. ruthenium, rhodium, palladium, osmium, iridium and platinum or metals such as copper, silver, gold, iron, cobalt and nickel. Palladium, platinum and ruthenium are preferably used.

Said catalysts are preferably used on carrier materials such as carbon, aluminium oxide, silicic acid, magnesium oxide, calcium oxide, titanium oxide and asbestos or a mixture of two or more of said carriers. Palladium on carbon has proved especially advantageous. The concentration of the catalyst preferably is in the range of from 0.02 to 20% by weight, calculated on the carrier material, preferably of from 0.1 to 10% by weight.

The process may be effected in the liquid or in the gaseous phase, continuously or discontinuously.

In the liquid phase it is generally operated at temperatures of from 160° to 350° C and under pressure sufficient for maintaining the liquid phase. Temperatures of from 180° to 250° C are preferably used, as an especially high selectivity is obtained at these temperatures, while the dehydrogenation is effected very quickly.

It is important to maintain a low hydrogen partial pressure, owing to the fact that the equilibrium thus is shifted towards the dehydrogenation and a hydrogenation or a hydrogenolysis of the starting compounds and final products is dispensed with. Such a low hydrogen partial pressure may be obtained by flushing the reactor system with an inert gas and by maintaining a pressure slightly in excess to the vapor pressure of the solvent.

A solvent is preferably used, owing to the fact that the selectivity of the reaction may thus be improved. To obtain a maximum selectivity there are used from 20 to 95% by weight of solvent, calculated on the weight of the starting material.

Among the solvents preferred for this reaction there may be mentioned aromatic hydrocarbons such as benzene, toluene, xylene, pseudocumene, naphtalene, anthracene, biphenyl, decaline, tetraline; aromatic and aliphatic ethers such as diphenyl ethers, diethylene glycol diethyl ethers or triethylene glycol diethyl ethers as well as generally di- or triethylene glycol dialkyl ethers containing alkyls having up to 6 carbon atoms. Further suitable solvents, for example, are water, alcohols, especially ethylene glycol, propylene glycol, ketones such as, acetone, methyl ethyl ketone, phenol or even the final product.

When carrying out the process in the gaseous phase there may be used a carrier gas such as nitrogen or hydrogen or readily volatile solvents such as alcohols, ethers, acetic acid or acetone may be admixed to the starting material. Water has proved especially advantageous, as it considerably improves the selectivity of the resorcinol monoalkyl ether formation by suppressing the formation of phenol. The temperature and the retention time required for dehydrogenizing depending on the composition of the feed and the catalyst used may vary within wide limits, as in the case of the liquid phase. Generally it is operated at temperatures of from 180° to 450° C, preferably of from 200° to 300° C continuously or discontinuously and at subatmospheric pressure or at atmospheric pressure, but it is also possible to operate at higher pressures, for example up to 10 atmospheres gauge, provided that the $H_2$ partial pressure is maintained at a low level. An especially advantageous pressure is in the range of from 0.5 to 5 atmospheres gauge.

The 3-alkoxycyclohexenones used as starting compounds are known or may be prepared in known manner by reacting cyclohexanediones-(1,3) with the corresponding alcohols, preferably in the presence of acid catalysts. The water formed thereby is separated azeotropically; suitable azeotrope forming agents for water, for example, are benzene, cyclohexane or toluene. The end of the etherification process may be seen by the fact that the aqueous phase is not separated any longer. In case that an unsoluble acid catalyst is used (for example an acid ion exchanger) this is filtered off and the desired 3-alkoxy-cyclohexene-(2)-one-(1) is obtained by distillation or crystallization in a high purity and a high yield.

As cyclohexanediones-(1,3) are present in the enol form as 3-hydroxy-cyclohexene-(2)-ones-(1) which constitute vinylogous acids, 3-alkoxy-cyclohexene-(2)-ones-(1) may already be formed without adding an acid catalyst. 3-Methoxy-cyclohexene-(2)-one-(1), for example, is already formed, when a methanolic solution of cyclohexanedione is allowed to stand at room temperature.

The 3-alkoxy-cyclohexene-(2)-ones-(1) may then be dehydrogenized in the above manner described. The resorcinol monoethers formed are purified by distillation.

The following examples illustrate the invention:

a. Preparation of 3-alkoxycyclohexene-(2)-ones

EXAMPLES 1 to 6 (cf. Table 1)

1 mole of a cyclohexanedione obtained from the corresponding 5-oxo-hexanoic acid ester according to German Offenlegungsschrift No. 2,245,270 was allowed to boil at the reflux together with 1 to 5 moles of a monofunctional alcohol or 0.5 mole of a diol and 10 g of an acid ion exchanger in the 3 to 6 fold quantity of an azeotrope forming agent (calculated on the total quantity of cyclohexanedione and alcohol). The water formed was distilled off azeotropically over a column. In the condensation and cooling process the distillate separated into two phases: an upper organic phase which is recycled continuously and a lower aqueous phase containing-in the case of isopropanol-water-benzene-about 85% of water, 14% of isopropanol and 0.5% of benzene.

When no more water separated the distillation residue was allowed to cool, the catalyst was filtered off and the excess of alcohol and azeotrope forming agent was removed at atmospheric pressure. The desired 3-alkoxycyclohexenone was obtained subsequently by fractionating in vacuo in Examples 1 to 4. A small quantity of distillation residue substantially contained unreacted cyclohexanedione. The reaction products crystallized in Examples 5 and 6 when cooling and were purified by recrystallization.

In the preparation of n-butoxy-cyclohexene-(2)-one an azeotrope forming agent was not required, owing the fact that n-butanol already forms an azeotrope with water which separated when cooling into two phases, whereof the organic phase was recycled.

The reaction products II' of diols with cyclohexanediones already crystallized in a high purity when cooling the distillation residue after the water had been separated.

b. Dehydrogenation of the 3-alkoxy-cyclohexene-(2)-ones to yield resorcinol monoethers in the liquid phase:

EXAMPLES 7 to 12 (cf. Table 2)

In a 250 ml three-necked flask provided with a reflux cooler, a magnetic stirrer and a thermometer a mixture of 100 ml of solvent and 2 g of dehydrogenation catalyst (0.2 g of Pd per 1.8 g of active carbon) were heated while stirring and flushing with nitrogen to a temperature of from 180° to 220° C. 10 to 20 g of the alkoxycyclohexenones to be dehydrogenized were then added within 1 hour. The quantity of hydrogen formed in the dehydrogenation was determined by means of a gasometer. The temperature was maintained while adding said substance in a range of from 180° to 220° C. When terminating the addition of alkoxycyclohexenone the temperature still was maintained at a level of from 200° to 220° C for a short period until no more was formed. Then the whole was cooled while flushing it with nitrogen, the catalyst was filtered off and the filtrate was distilled in vacuo. The corresponding resorcinol monoether was obtained after having fractionated the solvent. In Examples 11 and 12 the remaining reaction products were obtained in a pure form from a solvent by crystallization after having removed the polyglycol ether.

All known product were identified by the boiling point and the nuclear magnetic resonance spectrum, all new products by the nuclear magnetic resonance spectrum and a C – H analysis.

c. Dehydrogenation of the 3-alkoxycyclohexene-(2)-ones in the gaseous phase

EXAMPLES 13 to 20 (cf. Table 3)

A mixture of an 3-alkoxycyclohexenone and water was introduced dropwise into an evaporator preheated to 350° C and the vapors were passed over a dehydrogenation catalyst heated to a temperature of from 200° to 280° C.

The quantity of hydrogen formed was determined by means of a gasometer. At the outlet of the reactor the product was condensed; two phases formed while cooling. The lower organic phase essentially consisted of resorcinol monoether and unreacted alkoxycyclohexenone. The aqueous phase contained small quantities of resorcinol and phenol. After having separated the phases, the reaction products obtained were worked up by distillation.

TABLE 1:

EXAMPLES 1 to 6:
Preparation of 3-alkoxy-cyclohexane-(2)-ones

| Ex. | cyclo-hexane-dione (1,3) (g) | alcohol (ml) | azeotrope fromimg agent (ml) | acid ion ex-changer (Amberlist(R)15) (g) | tem-pera-ture (° C) | reac-tion time (hours) |
|---|---|---|---|---|---|---|
| 1 | 22.4 | methanol (150) | — | 5 | 25 | 1 |
| 2 | 56 | 2-propanol (150) | benzene (200) | 1 | 66 | 40 |
| 3 | 353 | n-butanol (2000) | — | 20 | 93 | 3 |
| 4 | 100 | allyl alcohol (300) | toluene (200) | 10 | 81 | 2 |
| 5 | 112 | 1,4-butanediol (45) | toluene (200) | 10 | 81 | 6 |
| 6 | 112 | diglycol (53) | toluene (200) | 10 | 109 | 5 |

| Ex. | structure | | Product boiling point mm HG | ° C | yield (g) | (% of the theory) |
|---|---|---|---|---|---|---|
| 1 | R:—CH$_3$ | | 3 | 93 | 23.9 | 95 |
| 2 | R:—CH(CH$_3$)$_2$ | | 5 | 110–112 | 50 | 65 |
| 3 | R:—CH$_2$)$_3$CH$_3$ | | 10 | 142 | 400 | 76 |
| 4 | R:—CH$_2$—CH=CH$_2$ | | 5 | 122 | 95 | 70 |
| 5 | 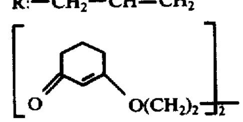 | | melting point 145° (acetonitrile) | | 92 | 66 |
| 6 | 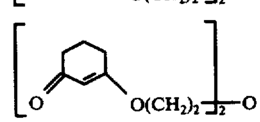 | | melting point 115° (ethylacetate) | | 115 | 78 |

TABLE 2:

EXAMPLES 7 to 12:
Dehydrogenation of the 3-alkoxycyclohexene(2)-ones[1]
in the liquid phase to yield resorcinol monoethers

| | starting material | | reaction conditions | | | product | | | boiling point | |
| | structure | quan-tity | reaction time | solvent | | temp. | structure | yield | | | |
| Ex. | | (g) | (min.) | (nature) | (ml) | (° C) | | (g) | (%) | mmHg | ° C |
| 7 | R: —(CH$_2$)$_3$CH$_3$ | 40 | 240 | — | — | 220 | R: cf. starting material | 24 | 60 | 2 | 130 |
| 8 | R: —(CH$_2$)$_3$CH$_3$ | 10 | 60 | PGE[2] | 50 | 215 | | 9.4 | 95 | 2 | 130 |

TABLE 2:-continued

EXAMPLES 7 to 12:
Dehydrogenation of the 3-alkoxycyclohexene(2)-ones[1] in the liquid phase to yield resorcinol monoethers

| Ex. | starting material structure | quantity (g) | reaction time (min.) | solvent (nature) | (ml) | temp. (°C) | product structure | yield (g) | (%) | boiling point mmHg | °C |
|---|---|---|---|---|---|---|---|---|---|---|---|
| 9 | R: —CH$_3$ | 12.6 | 60 | PGE | 50 | 220 | " | 11.7 | 94 | 5 | 102 |
| 10 | R: —CH$_2$—CH=CH$_2$ | 16.2 | 60 | PGE | 50 | 190 | " | 10.0 | 63 | 2 | 120 |
| 11 | (bis structure, (CH$_2$)$_4$ linker) | 10 | 60 | PGE | 50 | 215 | (bis resorcinol ether, (CH$_2$)$_4$ linker) | 9.5 | 95 | | melting point 104° (acetone) |
| 12 | (tris structure, (CH$_2$)$_2$—O—(CH$_2$)$_2$ linkers) | 34.0 | 120 | PGE | 100 | 215 | (tris resorcinol ether, (CH$_2$)$_2$—O—(CH$_2$)$_2$) | 23 | 70 | | melting point 122° (ethyl acetate/hexane) |

[1]catalyst: 0.1 g of Pd on 0.9 g of carbon as carrier material
[2]PGE = triethylene glycol diethyl ether

TABLE 3:

EXAMPLES 13 to 20:
3-Resorcinol monobutyl ethers (RBE) obtained by dehydrogenation of 3-n-butoxycyclohexene-(2)-one (BCH) in the gaseous phase

| Example | catalyst (100 ml) | temp. (°C) | feed BCH (g/h) | feed H$_2$O (g/h) | feed H$_2$ (l*/hours) | conversion BCH (% by weight) | selectivity (mole %) RBE | phenol | resorcinol | space-time-yield (g RBE/1 · h) |
|---|---|---|---|---|---|---|---|---|---|---|
| 13 | 2% Pd/C | 220 | 22.5 | — | 34 | 100 | — | 46 | — | — |
| 14 | " | 220 | 22.5 | 22.5 | 34 | 100 | 50 | 15 | 3.0 | 112 |
| 15 | 10% Pd/C | 205 | 22.5 | 22.5 | — | 100 | 60.5 | 7.5 | — | 135 |
| 16 | " | 200 | 45 | 22.5 | — | 97 | 83 | 3.0 | 3.5 | 370 |
| 17 | " | 200 | 90 | 45 | — | 48.5 | 90 | 2.0 | 2.0 | 390 |
| 18 | " | 240 | 60 | 22.5 | — | 95.6 | 91.5 | 1.5 | 2.0 | 525 |
| 19 | " | 280 | 84 | 45 | — | 78.6 | 88.5 | 2.0 | 1.8 | 565 |
| 20 | 2% Pd/SiO$_2$ | 260 | 45 | 22.5 | — | 45.7 | 62 | 3.0 | 4.0 | 123 |

*liters (under standard conditions)

What is claimed is:

1. A process for the preparation of resorcinol monoalkyl ethers of the general formula I and II:

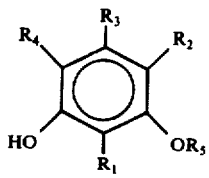

I

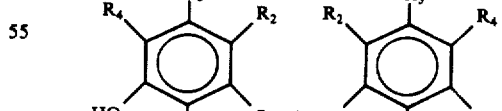

II

-continued wherein the radicals R$_1$ to R$_4$ may be the same or different and each represents a hydrogen, straight chain, branched or cyclic aliphatic radical or an aryl group or araliphatic radical and the radicals R$_5$ and A stand for straight chain, branched or cyclic aliphatic radical or araliphatic radical which comprise dehydrogenating in a liquid phase using as a liquid a triethylene glycol dialkyl ether or a diethylene glycol dialkyl ether having alkyl groups of up to 6 carbon atoms, at a temperature from 160° to 350° C in the presence of a catalyst containing noble metals of subgroup VIII of the Periodical Table 3-alkoxycyclohexene-(2)-ones of the general formulae I' and II"
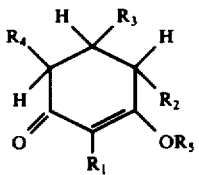
I'
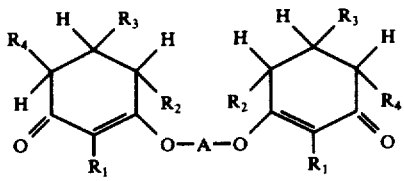
II'
wherein $R_1$ to $R_5$ and A have the aforesaid meaning.
* * * * *